(12) United States Patent
Haile et al.

(10) Patent No.: US 8,563,722 B2
(45) Date of Patent: Oct. 22, 2013

(54) STEREOSELECTIVE HYDROGENATION OF A KETONE

(75) Inventors: Pamela A. Haile, Collegeville, PA (US); Clark A. Sehon, Collegeville, PA (US); Huan Wang, King of Prussia, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 153 days.

(21) Appl. No.: 13/202,834

(22) PCT Filed: Feb. 23, 2010

(86) PCT No.: PCT/US2010/025020
§ 371 (c)(1),
(2), (4) Date: Aug. 23, 2011

(87) PCT Pub. No.: WO2010/099098
PCT Pub. Date: Sep. 2, 2010

(65) Prior Publication Data
US 2011/0306765 A1    Dec. 15, 2011

Related U.S. Application Data

(60) Provisional application No. 61/154,850, filed on Feb. 24, 2009.

(51) Int. Cl.
*C07D 471/10* (2006.01)

(52) U.S. Cl.
USPC .......................................................... 546/18

(58) Field of Classification Search
USPC .......................................................... 546/18
See application file for complete search history.

(56) References Cited

U.S. PATENT DOCUMENTS

| | | |
|---|---|---|
| 7,488,833 B2 | 2/2009 | Kralik et al. |
| 2007/0197590 A1 | 8/2007 | DeMong et al. |
| 2008/0318990 A1 | 12/2008 | Eidam et al. |

OTHER PUBLICATIONS

Chemler et al. "Product subclass 8 . . ." CA149:128422 (2006).*
Zanotti-Gerosa, et al., Ruthenium-Catalysed Asymmetric Reduction of Ketones—Diphosphine Ligands in Hydrogenations for Pharmaceutical Synthesis, Platinum Metals Rev, 49(4):158-165 (2005).

* cited by examiner

*Primary Examiner* — Celia Chang
(74) *Attorney, Agent, or Firm* — Bonnie L. Deppenbrock

(57) ABSTRACT

The present invention relates to a method comprising reducing a ketone of formula I:

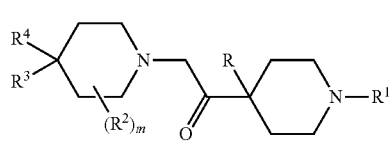

with an enantioselective hydrogenating agent to form substantially enantiomerically pure alcohol of formula II:

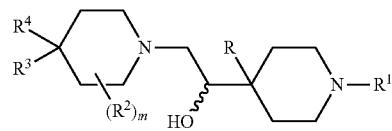

where R—R$^4$ and m are as defined herein. The method of the present invention is useful for making CCR2 modulators as wells as precursors CCR2 modulators.

4 Claims, No Drawings

STEREOSELECTIVE HYDROGENATION OF A KETONE

This application is filed pursuant to 35 U.S.C. §371 as a U.S. National Phase Application of International Patent Application Serial No. PCT/US2010/025020 filed Feb. 23, 2010, which claims priority to U.S. Application No. 61/154,850 filed Feb. 24, 2009, the contents of which are incorporated herein by reference.

BACKGROUND OF THE INVENTION

The present invention relates to a method of stereoselectively hydrogenating a ketone that is particularly useful as an intermediate for a CCR2 antagonist.

CCR2 is a chemokine receptor that is expressed on a cell surface of monocycles and some other blood leukocytes. CCR2 binds to the monocyte chemotactic protein MCP-1, and other CC chemokines, which are produced at sites of inflammation and infection. Recruitment of monocytes to inflammatory sites by MCP-1/CCR2 interactions has been implicated in driving the pathogenesis of a number of diseases including multiple inflammatory disorders including rheumatoid arthritis, atherosclerosis, multiple sclerosis, bronchiolitis obliterans syndrome, asthma, allergic rhinitis, eczema, atopic dermatitis, kidney disease, alveolitis, nephritis, liver cirrhosis, congestive heart failure, viral meningitis, cerebral infarction, neuropathy, Kawasaki disease, Alzheimer's disease, stroke, acute nerve injury, HIV infection, AIDS, autoimmune diseases, cancer, sepsis, retinosis, inflammatory bowel disease, transplant arteriosclerosis, idiopathic pulmonary fibrosis, psoriasis, HIV-associated dementia, lupus, erthematosis, hepatitis, pancreatitis, Crohn's disease, endometriosis, metabolic syndrome, and diabetes.

A number of compounds in the art described as CCR2 antagonists contain a chiral hydroxyethylene group that links two piperidinyl groups. For example, US 2008/0318990 discloses CCR2 modulators that contain the following 1S enantiomeric fragment:

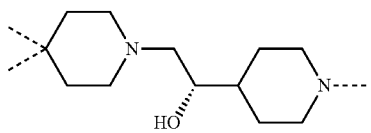

It would be desirable to discover a new way to prepare these chiral molecules.

SUMMARY OF THE INVENTION

The present invention relates to a method comprising reducing a ketone of formula I:

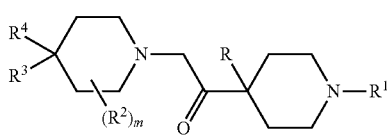

with an enantioselective hydrogenating agent to form a substantially enantiomerically pure alcohol of formula II:

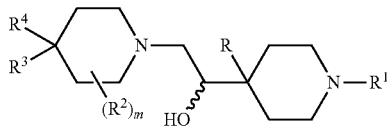

wherein R is H or OH;
$R^1$ is H, an amine protecting group,

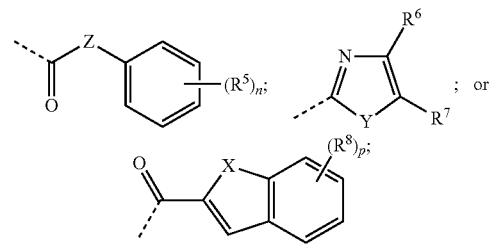

each $R^2$ is independently halo, methyl, hydroxy, or hydroxymethyl;
$R^3$ is H and $R^4$ is phenyl-$(R^5)_n$, indolyl-$(R^8)_p$, 1-H-pyrrolo[2,3-b]pyridine-3-yl-$(R^8)_p$, benzimidazolyl-$(R^8)_p$, benzoxazolyl-$(R^8)_p$, or pyrazolyl; or
$R^3$ and $R^4$, together with the carbon atom to which they are attached form a spiroindolinyl, a spiroindanyl, a spiroindenyl, or a spirodihydrobenzoxazolyl group, each optionally substituted with up to three substituents selected from the group consisting of halo, CN, $C_1$-$C_6$-alkyl, $C_1$-$C_6$-alkoxy, hydroxy, hydroxymethyl, trifluoromethyl, trifluoromethoxy, $SO_2CH_3$, $(R^5)_n$-phenoxy-, $(R^5)_n$-benzyloxy-, $C(O)N(R^9)_2$, and COOH;
each $R^5$ is independently halo, CN, $C_1$-$C_6$-alkyl, $C_1$-$C_6$-alkoxy, hydroxy, hydroxymethyl, trifluoromethyl, trifluoromethoxy, $SO_2CH_3$, phenyl, $C(O)N(R^9)_2$, or COOH;
$R^6$ and $R^7$ are each independently H, $C_1$-$C_6$ alkyl, phenyl-$(R^5)_n$, heteroaryl-$(R^8)_p$, $CON(R^9)_2$, CN, COOH, COOCH$_3$, COOCH$_2$CH$_3$, or $R^6$ and $R^7$, together with the carbon atoms to which they are attached, form a fused benzo group;
each $R^8$ is independently halo, amino, cyano, $C_1$-$C_6$-alkyl, $C_1$-$C_6$-alkoxy, —NHSO$_2$CH$_3$, —NHC(O)CH$_3$, $C_5$-$C_6$-heterocycloalkyl, hydroxy, hydroxymethyl, trifluoromethyl, trifluoromethoxy, $SO_2CH_3$, $C(O)N(R^{10})_2$, $(R^{10})_r$-phenoxy-, $(R^{10})_r$-benzyloxy-, or COOH;
each $R^9$ is independently H or $C_1$-$C_6$-alkyl or, together with the nitrogen atom to which they are attached, form a $C_5$-$C_6$-heterocycloalkyl group;
each $R^{10}$ is independently halo, CN, $C_1$-$C_6$-alkyl, $C_1$-$C_6$-alkoxy, hydroxy, hydroxymethyl, trifluoromethyl, trifluoromethoxy, or $SO_2CH_3$;
Y is O or S;
X is NH, N—CH$_3$, O, or S;
Z is —NH— or

m is 0, 1, or 2;
each n is independently 0, 1, 2, or 3; and
each p is independently 0, 1, 2, or 3.

The method of the present invention provides a way of converting a ketone to a substantially enantiomerically pure chiral compound, which is either useful as a CCR2 modulator or a precursor to a CCR2 modulator.

DETAILED DESCRIPTION OF THE INVENTION

The present invention relates to a method comprising reducing a ketone of formula I:

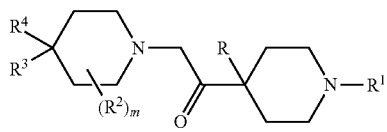

I with an enantioselective hydrogenating agent to form substantially enantiomerically pure alcohol of formula II:

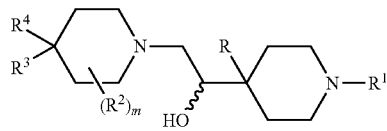

where R—$R^4$ and m are as previously defined.

In another aspect, the enantioselective hydrogenating reagent is a bisphosphino-ruthenium or bisphosphino-diamine-ruthenium complex.

In another aspect, the enantioselective hydrogenating reagent is selected from the group consisting of:

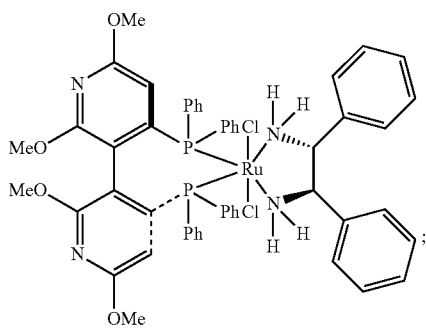

;

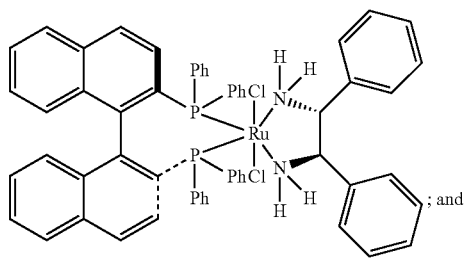

; and

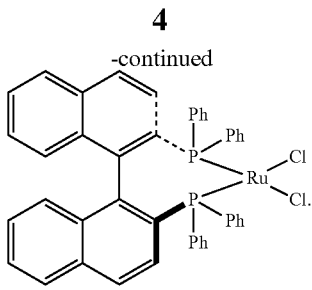

In another aspect, $R^1$ is a BOC or CBz group.
In another aspect, $R^1$ is

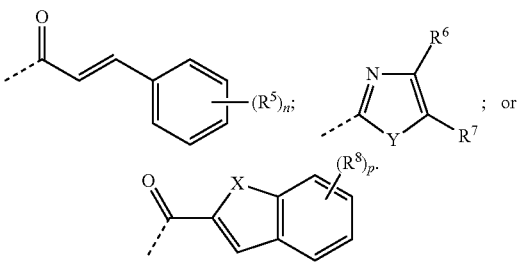

; or

In another aspect, $R^1$ is

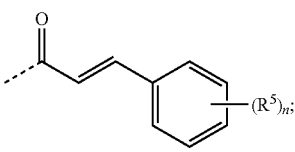

where each $R^5$ is independently F, Cl, Br, $CF_3$, $CH_3$, benzyloxy, or $OCH_3$; and
n is 0, 1, or 2.
In another aspect, $R^1$ is:

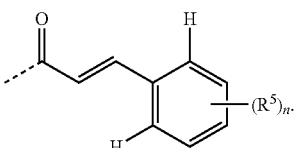

In another aspect, $R^1$ is:

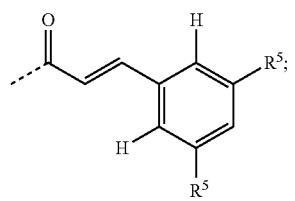

wherein each $R^5$ is independently F or Cl.
In another aspect, $R^3$ is H and $R^4$ is phenyl-$(R^5)_n$, indol-3-yl-$(R^8)_p$, 1-H-pyrrolo[2,3-b]pyridine-3-yl-$(R^8)_p$, benzimidazol-2-yl-$(R^8)_p$, benzoxazol-2-yl-$(R^8)_p$, or pyrazol-3-yl; each $R^8$ is independently amino, —$NHSO_2CH_3$, —$NHC(O)CH_3$, methyl, methoxy, trifluoromethoxy, benzyloxy, phenoxy, cyano, morpholino, fluoro, or chloro; and p is 0, 1, or 2.

In another aspect, $R^3$ and $R^4$, together with the carbon atom to which they are attached, form an optionally substituted spiroindolinyl, a spiroindanyl, a spiroindenyl, or a spirodihydrobenzoxazolyl group.

In another aspect, $R^3$ and $R^4$, together with the carbon atom to which they are attached form an optionally substituted spiroindolinyl group optionally substituted with up to two substituents selected from the group consisting of $CH_3$, F, Cl, and CN.

In another aspect, the present invention is a method comprising reducing a ketone of the following formula:

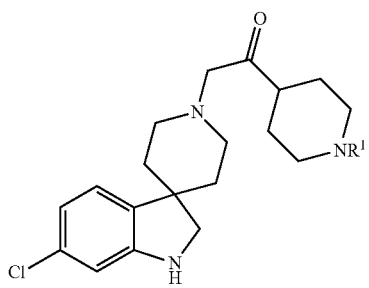

with an enantioselective ruthenium phosphine hydrogenating agent to form a substantially enantiomerically pure alcohol having the following formula:

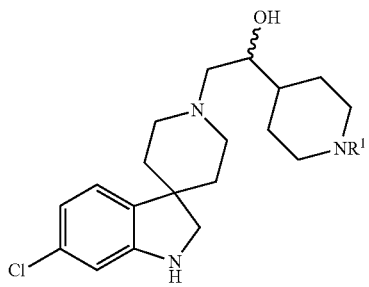

wherein $R^1$ is Cbz or BOC.

In another aspect the ruthenium phosphine hydrogenating agent is

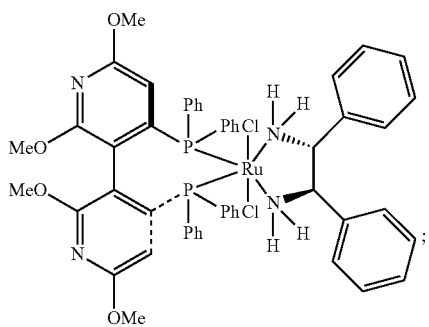

and the reduced compound has the following formula:

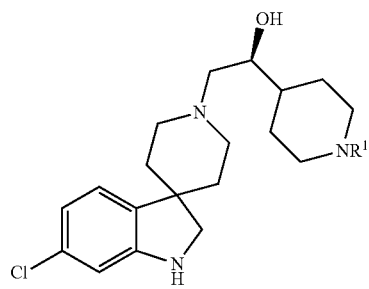

or a ditosylate salt thereof.

In another aspect, the reduced compound or ditosylate salt thereof is further reacted with a protic acid to form (1S)-2-(6-chloro-1,2-dihydro-1'H-spiro[indole-3,4'-piperidin]-1'-yl)-1-(4-piperidinyl)ethanol.

In another aspect, the (1S)-2-(6-chloro-1,2-dihydro-1'H-spiro[indole-3,4'-piperidin]-1'-yl)-1-(4-piperidinyl)ethanol is reacted with pentafluorophenyl (2E)-3-(3,5-difluorophenyl)-2-propenoate under such conditions to form (1S)-2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol.

The term "enantioselective hydrogenating agent" refers to a reagent that is used in the hydrogenation process that allows for the production of a substantially enantiomerically pure product, that is, a product that is at least 80%, preferably at least 90%, and most preferably at least 95% enantiomerically pure. Examples of enantioselective hydrogenating agents are bisphosphino-diamine-ruthenium complexes A and B and bisphosphino ruthenium complex C:

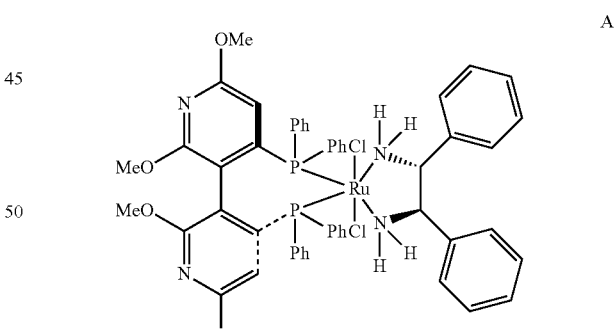

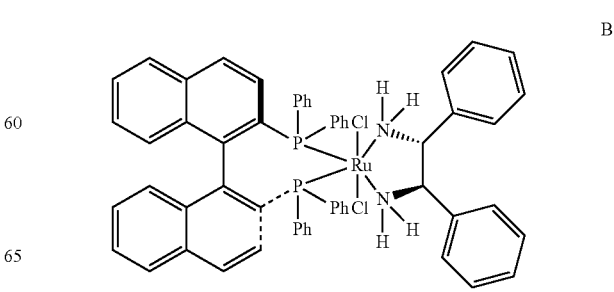

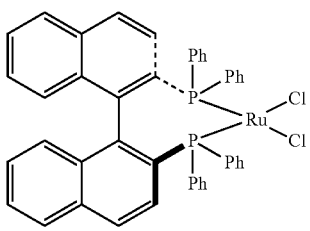

Catalyst A is dichloro[(R)-(+)-2,2',6,6'-tetramethoxy-4,4'-bis(diphenylphosphino)-3,3'-bipyridine][(1R,2R)-(+)-1,2-diphenylethylenediamine]ruthenium(II)

Catalyst B is dichloro[(R)-(+)-2,2'-bis(diphenylphosphino)-1,1'-binaphthyl][(1R,2R)-(+)-1,2-diphenylethylenediamine]ruthenium(II)

Catalyst C is dichloro[(S)-(−)-2,2'-bis(diphenylphosphino)-1,1'-binaphthyl]ruthenium(II)

The term "amine protecting group" refers to a group that protects the amine to which it is attached against possible competitive reactions. Examples of suitable amine protecting groups include carbobenzyloxy (CBz), t-butoxycarbonyl (BOC), p-methoxybenzylcarbonyl (MOZ), benzyl, p-methoxybenzyl (PMB), and 3,4-dimethoxybenzyl (DMPM). CBz and BOC are particularly suitable.

The symbol:

is used to refer to a substantially enantiomerically pure form (either the S or the R form) of the compound.

As used herein, "$C_1$-$C_6$-alkyl" refers to straight or branched hydrocarbon chains containing the specified number of carbon atoms. Examples include methyl, ethyl, n-propyl, n-butyl, isobutyl, isopropyl, t-butyl, and 1,1-dimethylpropyl.

The term "halo" refers to fluoro, chloro, or bromo.

As used herein, "heteroaryl" refers to a 5- or 6-membered aromatic group that contains one or more heteroatoms selected from N, S, and O. Examples of heteroaryl groups include pyridinyl, furyl, thienyl, imidazolyl, pyrrolyl, pyrazolyl, oxazolyl, isoxazolyl, thiazolyl, isothiazolyl, triazolyl, tetrazolyl, and pyrimidinyl groups.

$R^6$ and $R^7$ may, together with carbon atoms to which they are attached, form a fused benzo group, as illustrated:

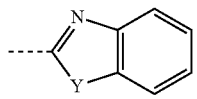

Representative examples of $C_5$-$C_6$-heterocycloalkyl groups include piperidinyl, piperazinyl, N-methylpiperazinyl, morpholino, and pyrrolidinyl groups. Each $R^9$, together with the nitrogen atom to which they are attached, may form such groups.

The following schemes are for illustrative purposes only and are not intended to limit the scope of this invention.

Scheme 1:

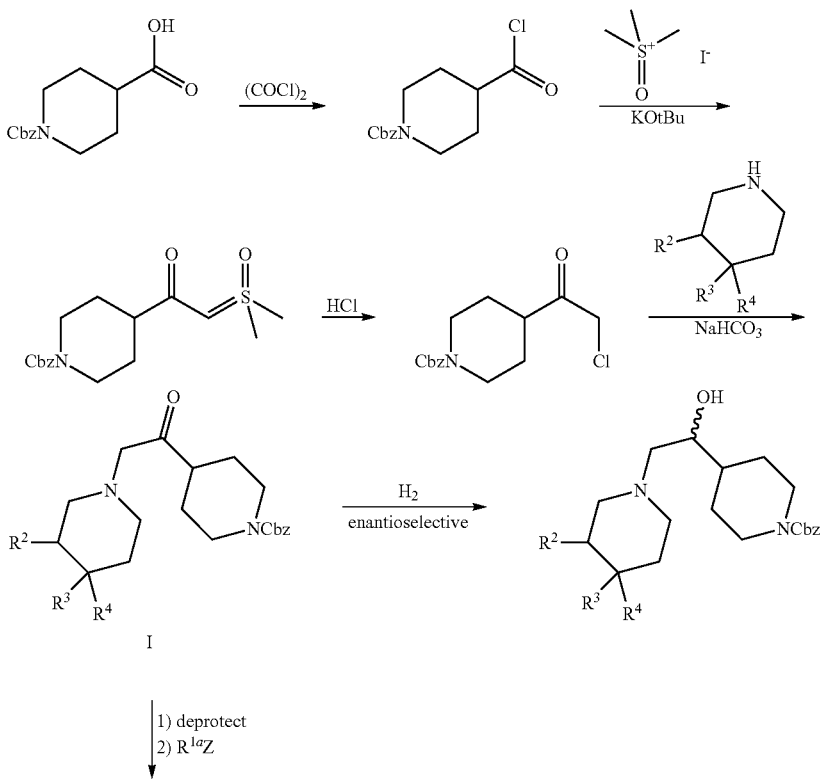

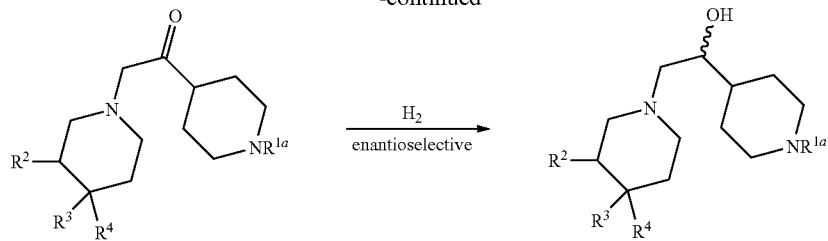

As Scheme 1 illustrates, a compound of formula I containing an amine protecting group such as Cbz can either be a) enantioselectively hydrogenated in a single step or b) deprotected (with a protic acid such as HCl) and coupled with $R^{1a}Z$ (where $R^{1a}$ is a subset of $R^1$ that excludes an amine protecting group or H; and Z is a suitable leaving group), before undergoing selective hydrogenation.

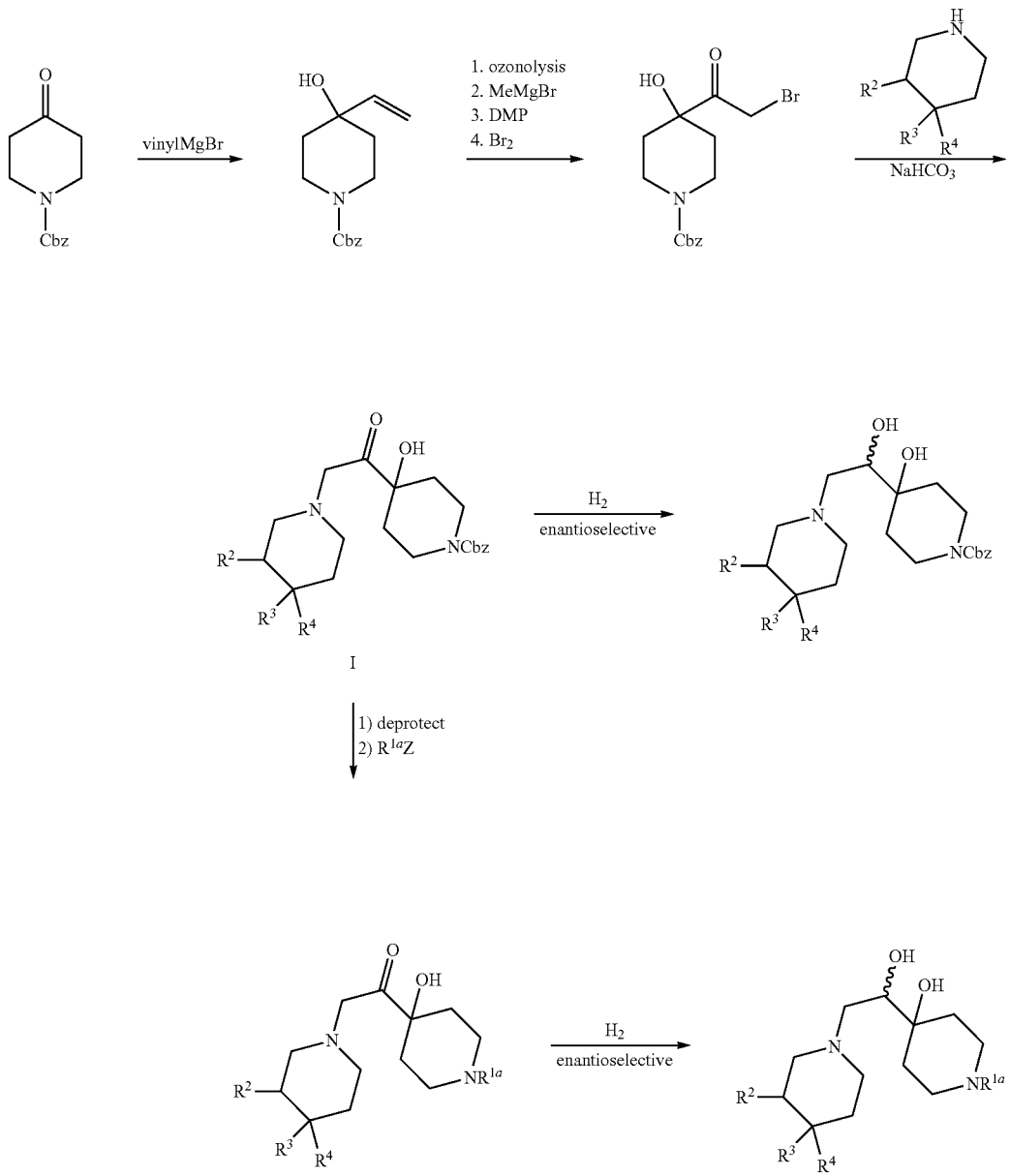

The following example is for illustrative purposes only and is not intended to limit the scope of the invention.

Preparation of phenylmethyl 4-[(1S)-2-(6-chloro-1,2-dihydro-1'H-spiro[indole-3,4'-piperidin]-1'-yl)-1-hydroxyethyl]-1-piperidinecarboxylate

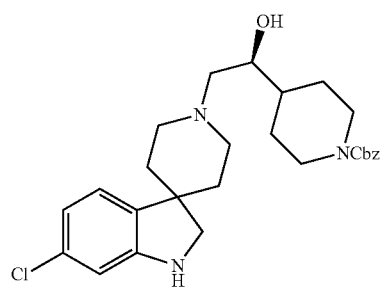 [SMILES: O=C(OCc1ccccc1)N1CCC([C@H](O)CN2CCC3(CC2)CNc2cc(Cl)ccc23)CC1]

A. Preparation of phenylmethyl 4-{[dimethyl(oxido)-1⁴-sulfanylidene]acetyl}-1-piperidinecarboxylate

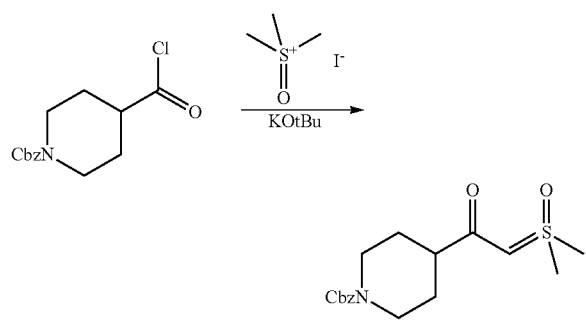

Trimethylsulfoxonium iodide (3.75 g, 17.0 mmol, 2.0 equiv.) and potassium tert-butoxide (2.22 g, 18.8 mmol, 2.2 equiv.) were dissolved in 30 mL of THF and heated to reflux for 3 h. The resultant suspension was cooled to 0° C., whereupon phenylmethyl 4-(chlorocarbonyl)-1-piperidinecarboxylate (2.4 g, 8.5 mmol, 1 equiv.) in 15 mL of THF was added dropwise. The mixture was stirred at 0° C. to room temperature for 3.5 h. CH$_2$Cl$_2$ (40 mL) and water (60 mL) were then added. The organic layer was separated, concentrated, and redissolved in 5 mL of refluxing EtOAc. Hexanes (10 mL) was added and the resultant suspension was cooled to room temperature overnight. The product was collected by filtration and dried under vacuum: 2.15 g, 6.37 mmol, 75%. ES-MS: m/z: 338 (M+H$^+$). $^1$H NMR δ ppm (CDCl$_3$, 300.13 MHz): 7.26-7.33 (m, 5H), 5.09 (s, 2H), 4.37 (s, 1H), 4.17 (br, 2H), 3.35 (m, 6H), 2.78 (m, 2H), 2.19 (tt, J=11.6, 3.6 Hz, 1H), 1.77 (d, J=12.4 Hz, 2H), 1.52 (ddd, J=24.4, 12.2, 3.6 Hz, 2H). $^{13}$C NMR δ ppm (CDCl$_3$, 75.48 MHz): 191.9, 155.0, 136.7, 128.3, 127.7, 127.6, 68.3, 66.8, 46.3, 43.7, 42.0, 28.7.

B. Preparation of phenylmethyl 4-[(6-chloro-1,2-dihydro-1'H-spiro[indole-3,4'-piperidin]-1'-yl)acetyl]-1-piperidinecarboxylate

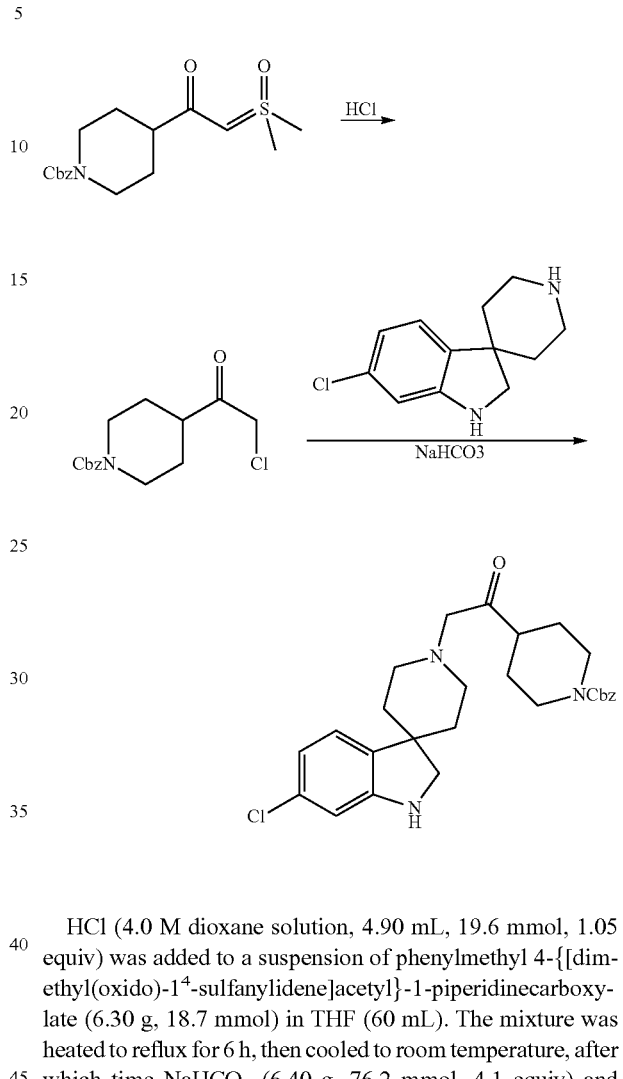

HCl (4.0 M dioxane solution, 4.90 mL, 19.6 mmol, 1.05 equiv) was added to a suspension of phenylmethyl 4-{[dimethyl(oxido)-1⁴-sulfanylidene]acetyl}-1-piperidinecarboxylate (6.30 g, 18.7 mmol) in THF (60 mL). The mixture was heated to reflux for 6 h, then cooled to room temperature, after which time NaHCO$_3$ (6.40 g, 76.2 mmol, 4.1 equiv) and 6-chloro-1,2-dihydrospiro[indole-3,4'-piperidine] (3.50 g, 15.7 mmol, 0.84 mmol) were then added. The mixture was heated to reflux for 20 h and cooled to room temperature, EtOAc (45 mL) and water (45 mL) were added, the organic layer separated, washed with NaHCO$_3$ (sat. aq., 45 mL), and concentrated. The residue was redissolved in EtOAc (30 mL) and added slowly to a solution of TsOH hydrate (6.67 g) in EtOH (6 mL)/EtOAc (30 mL) at reflux. The mixture was cooled to room overnight. The product (bistosylate of phenylmethyl 4-[(6-chloro-1,2-dihydro-1'H-spiro[indole-3,4'-piperidin]-1'-yl)acetyl]-1-piperidinecarboxylate) was collected by filtration and dried under vacuum: 7.52 g, 9.1 mmol, 58%. ES-MS: m/z: 482 (M+H$^+$). $^1$H NMR δ ppm (DMSO-d6, 300.13 MHz): 9.74 (br, 1H), 7.71 (br, 3H), 7.52 (d, J=8.0 Hz, 4H), 7.29-7.40 (m, 5H), 7.13 (d, J=7.9 Hz, 4H), 7.01-7.17 (m, 3H), 5.08 (s, 2H), 4.53 (br, 2H), 3.98 (m, 2H), 3.65 (s, 2H), 3.41 (d, J=9.9 Hz, 2H), 3.21 (m, 2H), 2.88 (br, 2H), 2.71 (tm, J=11.2 Hz, 1H), 2.29 (s, 6H), 2.19 (m, 2H), 1.84 (d, J=13.6 Hz, 4H), 1.36 (m, 2H).

C. Preparation of phenylmethyl 4-[(1S)-2-(6-chloro-1,2-dihydro-1'H-spiro[indole-3,4'-piperidin]-1'-yl)-1-hydroxyethyl]-1-piperidinecarboxylate

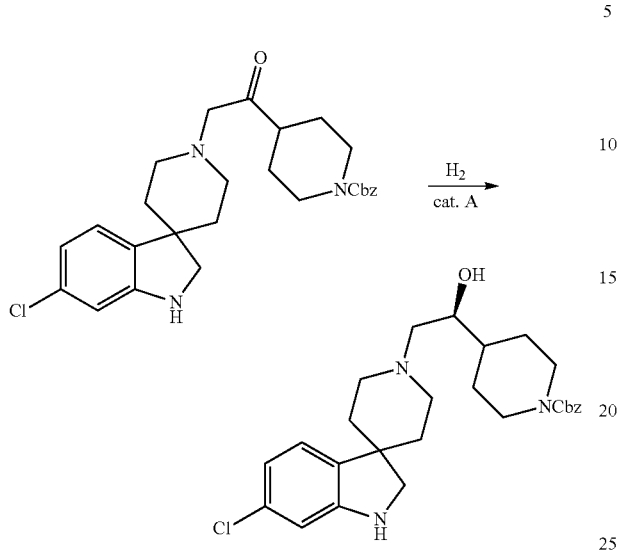

Aqueous NaOH (1 N, 10 mL) was added to a suspension of phenylmethyl 4-[(6-chloro-1,2-dihydro-1'H-spiro[indole-3,4'-piperidin]-1'-yl)acetyl]-1-piperidinecarboxylate bistosylate (672 mg, 0.813 mmol) CH$_2$Cl$_2$ (10 mL). The organic layer was washed with another portion of NaOH (1 N, 10 mL), separated, and concentrated. The residue was redissolved in EtOH (6 mL) with KOtBu (18.5 mg, 0.165 mmol, 0.2 equiv.) and added to 16.0 mg of catalyst A (0.017 mmol, 0.02 equiv.) The mixture was hydrogenated (150 psi, 35° C.) for 20 h, after which time the mixture was diluted with CH$_2$Cl$_2$ (15 mL) and washed with NaHCO$_3$ (sat. aq., 15 mL). The organic layer was concentrated, redissolved in 2 mL of EtOAc and added to TsOH hydrate (369.8 mg) in EtOH (0.4 mL)/EtOAc (2 mL) at reflux. The mixture was heated at reflux for 2 h, then cooled to room temperature overnight. The bitosylate of the product was isolated by filtration and dried under vacuum: 492 mg, 0.594 mmol, 73%, 97.3% ee. ES-MS: m/z: 484 (M+H$^+$). $^1$H NMR δ ppm (DMSO-d6, 300.13 MHz): 9.08 (br, 1H), 7.50 (d, J=8.0 Hz, 4H), 7.29-7.40 (m, 5H), 7.12 (d, J=8.0 Hz, 4H), 7.01 (d, J=7.9 Hz, 1H), 6.83-6.90 (m, 2H), 5.07 (s, 2H), 4.04 (m, 2H), 3.73 (m, 1H), 3.03-3.57 (m, 8H), 2.75 (br, 2H), 2.28 (s, 6H), 2.19 (m, 1H), 1.98 (m, 1H), 1.80 (m, 3H), 1.51 (m, 2H), 1.17 (m, 2H).

What is claimed is:

1. A method comprising reducing a ketone of the following formula:

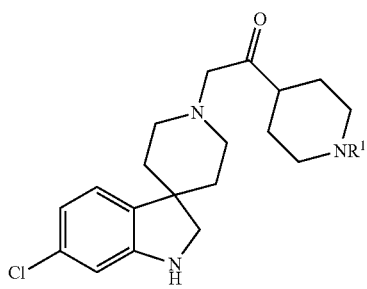

with an enantioselective ruthenium phosphine hydrogenating agent to form a substantially enantiomerically pure alcohol having the following formula:

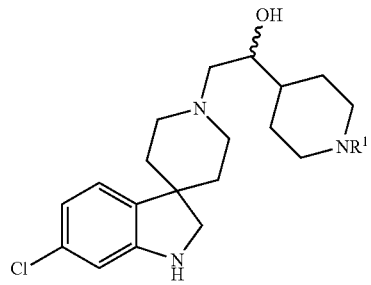

wherein R$^1$ is Cbz or BOC.

2. The method of claim 1 wherein the ruthenium phosphine hydrogenating agent is

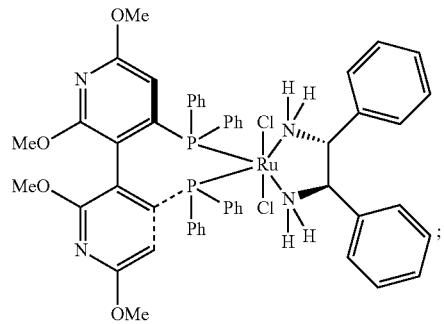

and the reduced compound has the following formula:

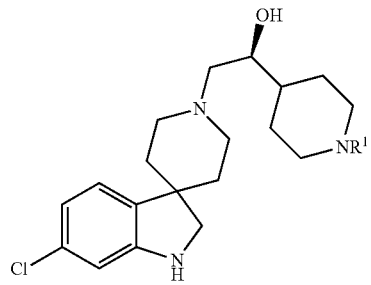

or a ditosylate salt thereof.

3. The method of claim 2 wherein the reduced compound or ditosylate salt thereof is further reacted with a protic acid to form (1S)-2-(6-chloro-1,2-dihydro-1'H-spiro[indole-3,4'-piperidin]-1'-yl)-1-(4-piperidinyl)ethanol.

4. The method of claim 3 wherein the (1S)-2-(6-chloro-1,2-dihydro-1'H-spiro[indole-3,4'-piperidin]-1'-yl)-1-(4-piperidinyl)ethanol is reacted with pentafluorophenyl (2E)-3-(3,5-difluorophenyl)-2-propenoate under such conditions to form (1S)-2-(6-chloro-1,2-dihydro-4H-spiro[indole-3,4'-piperidin]-1'-yl)-1-{1-[(2E)-3-(3,5-difluorophenyl)-2-propenoyl]-4-piperidinyl}ethanol.

* * * * *